United States Patent
Reis et al.

(10) Patent No.: US 11,969,540 B2
(45) Date of Patent: Apr. 30, 2024

(54) MEDICAL IMPLEMENT FOR PROVIDING SUCTION AND IRRIGATION

(71) Applicant: BR SURGICAL, LLC, Jacksonville, FL (US)

(72) Inventors: Timothy J Reis, Jacksonville, FL (US); John Douglas Barrow, Tampa, FL (US); Michael J Ontiveros, Largo, FL (US)

( * ) Notice: Subject to any disclaimer, the term of this patent is extended or adjusted under 35 U.S.C. 154(b) by 0 days.

(21) Appl. No.: 18/175,448

(22) Filed: Feb. 27, 2023

(65) Prior Publication Data

US 2023/0277750 A1  Sep. 7, 2023

Related U.S. Application Data

(60) Provisional application No. 63/268,747, filed on Mar. 1, 2022.

(51) Int. Cl.
*A61M 1/00* (2006.01)

(52) U.S. Cl.
CPC ............ *A61M 1/774* (2021.05); *A61M 1/743* (2021.05)

(58) Field of Classification Search
CPC .......... A61M 2025/024; A61M 1/7413; A61M 1/774; A61M 1/772; A61M 1/77; A61M 1/76; A61M 1/743; A61B 2218/002; A61B 2218/007; A61B 2218/001
See application file for complete search history.

(56) References Cited

U.S. PATENT DOCUMENTS

| | | | | |
|---|---|---|---|---|
| 4,167,720 A | * | 9/1979 | Krasser | H01H 71/54 337/60 |
| 5,188,591 A | * | 2/1993 | Dorsey, III | A61M 1/774 604/35 |
| 5,203,769 A | | 4/1993 | Clement et al. | |
| 5,269,768 A | | 12/1993 | Cheung | |
| 5,295,956 A | * | 3/1994 | Bales | A61M 1/7415 606/49 |
| 5,303,735 A | | 4/1994 | Cerola et al. | |
| 5,322,503 A | * | 6/1994 | Desai | A61B 17/00234 606/49 |
| 5,336,220 A | * | 8/1994 | Ryan | A61M 5/1418 138/108 |
| 5,447,494 A | * | 9/1995 | Dorsey, III | A61M 1/774 604/38 |
| 5,449,145 A | * | 9/1995 | Wortrich | F16K 27/041 D23/245 |
| 5,484,402 A | * | 1/1996 | Saravia | A61M 1/7415 604/35 |
| 5,522,796 A | | 6/1996 | Dorsey, III | |

(Continued)

*Primary Examiner* — Scott J Medway
(74) *Attorney, Agent, or Firm* — Mark Young, P.A.

(57) ABSTRACT

A suction and irrigation implement includes a handpiece, a pair of aligned adjacent valve assemblies, a rocker and a hub. The body may be transparent to allow visualization of aspirated substances. The valve assemblies include a plunger with a conical core that increases the area of the valve opening with increased depression. The rocker, a pivoting actuator, opens one valve assembly at a time, thereby preventing simultaneous irrigation and suction. A suction and irrigation tube connects to the hub, which may be rotated to adjust the orientation of the tube, while the implement is in use. Detents define specific orientations.

11 Claims, 20 Drawing Sheets

(56) References Cited

U.S. PATENT DOCUMENTS

| | | | | |
|---|---|---|---|---|
| 5,830,214 | A | * | 11/1998 | Flom ................... A61B 18/1482 604/35 |
| 6,007,515 | A | * | 12/1999 | Epstein ............ A61B 17/00491 604/82 |
| 6,213,970 | B1 | * | 4/2001 | Nelson ................ A61M 3/0212 604/35 |
| 7,297,133 | B2 | | 11/2007 | Nelson et al. |
| 7,785,287 | B2 | * | 8/2010 | Reznik .................. A61M 3/022 601/2 |
| 7,867,196 | B1 | * | 1/2011 | Coplin ................ A61M 3/0258 604/131 |
| 8,052,644 | B2 | * | 11/2011 | Radgowski ............. A61M 1/77 604/118 |
| 2014/0207056 | A1 | * | 7/2014 | Bono .................... A61M 39/28 604/34 |
| 2015/0073364 | A1 | * | 3/2015 | Cheng ..................... A61M 1/74 604/319 |

\* cited by examiner

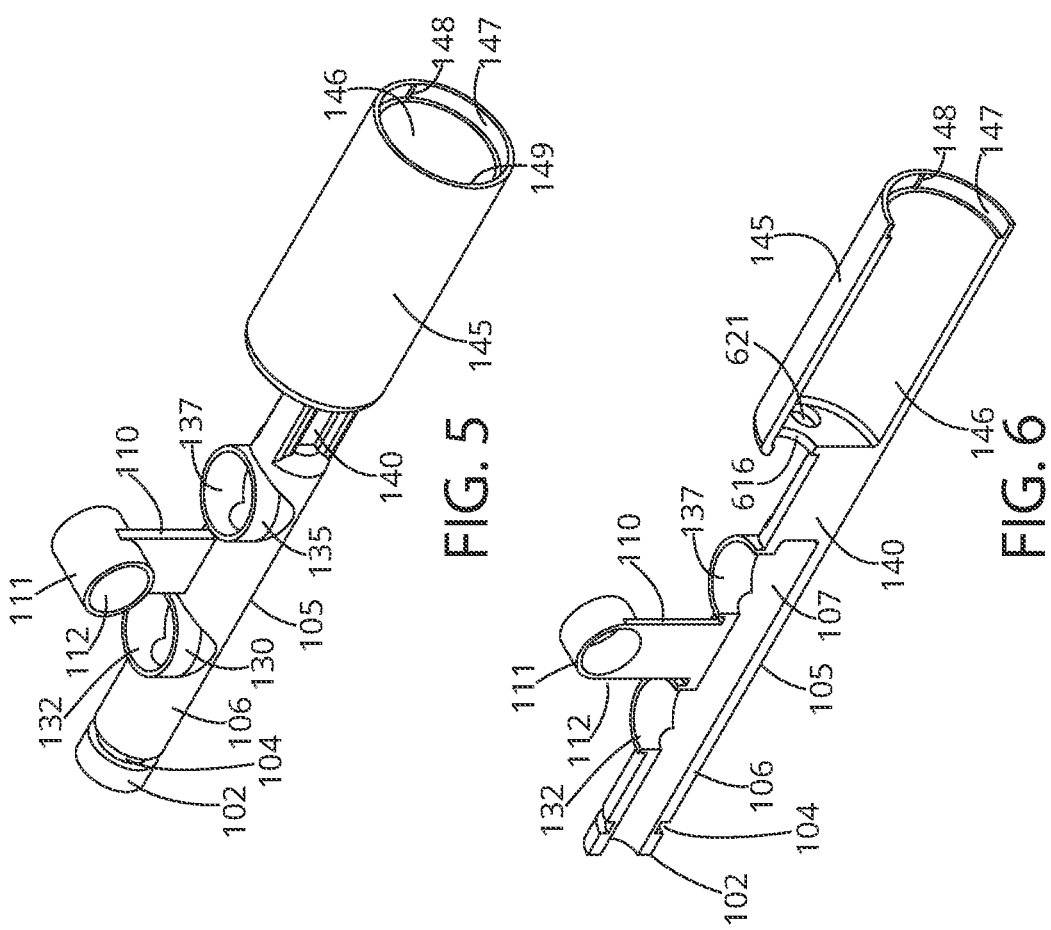

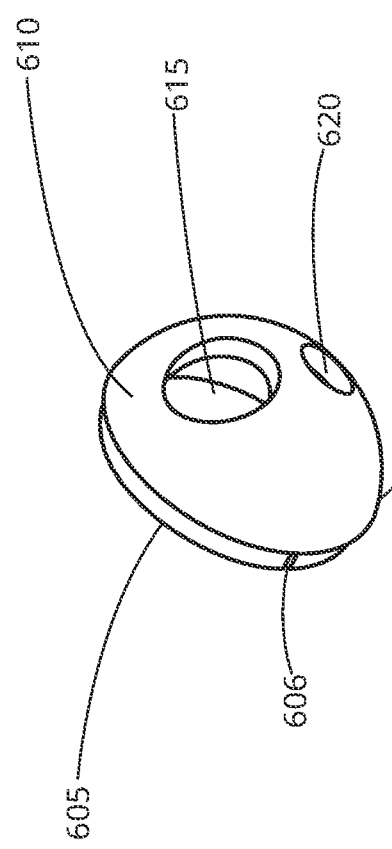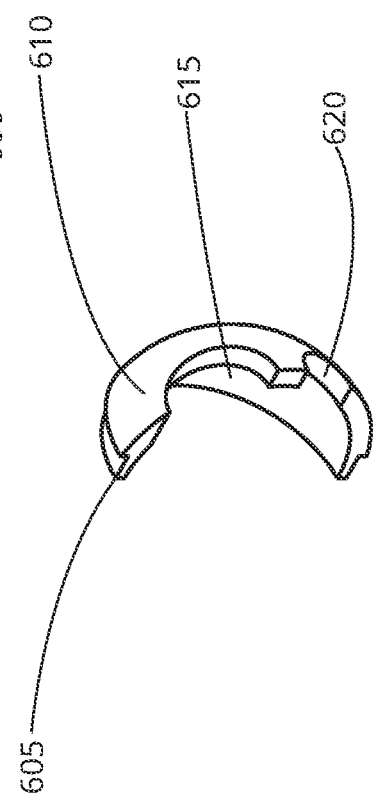

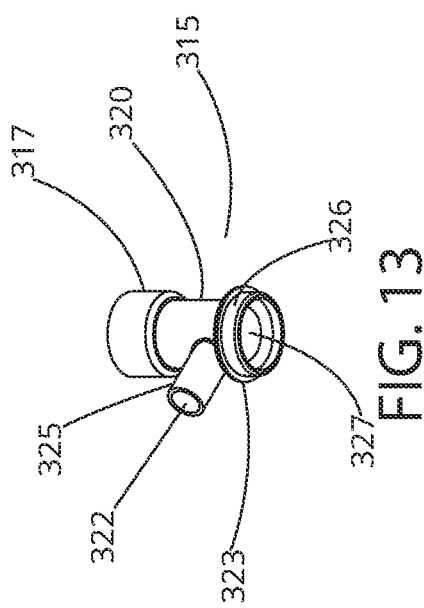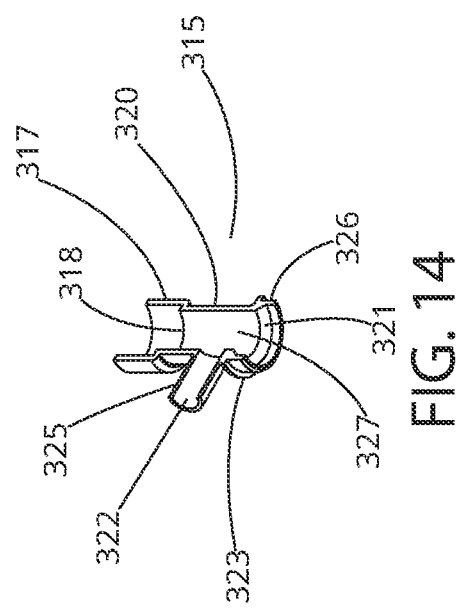

MEDICAL IMPLEMENT FOR PROVIDING SUCTION AND IRRIGATION

RELATED APPLICATION

This application is a nonprovisional of and claims the benefit of priority of U.S. provisional patent application Ser. No. 63/268,747 filed Mar. 1, 2022, the entire contents of which are incorporated herein by this reference.

FIELD OF THE INVENTION

This invention relates generally to a medical implement for irrigating and aspirating, and, more particularly, to a device for aspirating liquid and debris and irrigating with liquid during surgical and therapeutic procedures.

BACKGROUND OF THE INVENTION

Surgical and therapeutic procedures performed by medical practitioners, such as otolaryngologist (ENT) and neurosurgeons, entail aspirating liquid and debris and irrigating with liquid. By way of example and not limitation, nasal irrigation is an adjunctive therapy for upper respiratory conditions that bathes the nasal cavity with a liquid spray. The liquid may comprise water, a saline solution, a xylitol solution or some other cleansing, antiseptic or therapeutic composition.

Instruments for aspirating and irrigating include a suction port and an irrigation port. Separate valves control irrigation and suction. Each actuator, such as a button, trigger or knob, operates (i.e., controls opening and closing) a valve. This configuration allows the possibility of activating the valves simultaneously, which can produce an undesirable effect of aspirating (i.e., removing) irrigating liquid before the targeted region has been irrigated. Additionally, many such instruments locate the actuators apart, to reduce risk of mistake (i.e., mistakenly activating irrigation instead of suction). Often one actuator is more conveniently located than the other, thereby complicating manipulation and control.

Known irrigation instruments also provide limited flow control. The extent an actuator is actuated determines the flow rate. In many instruments, the flow rate is linearly related to said extent. For example, depressing a button ½ way produces a flow rate that is about 50% of the maximum flow rate. Problems arise when a low flow rate is desired or when an increasing or decreasing flow rate is desired. These flow rates can be difficult to achieve with a linear valve.

Known irrigation instruments are typically opaque. Thus, the liquid and entrained matter removed via suction are not visible to the practitioner. Without visibility, the practitioner cannot see if the effluent is clear or includes entrained blood, bio burden or infectious matter.

Known irrigation instruments do not facilitate changing the angle of the applicator tube. Such tubes come in various configurations, often with a curved free end. A practitioner's wrist allows a limited range of rotation. To reach certain portions of a cavity, the entire instrument is rotated. Such rotation is unwieldy and awkward, which compromises ease of use. Some instruments include a tube with a flexible tip and a malleable tube. While the tip may be bent in any direction, such bending is tedious and necessitates removing of the tube from the cavity.

An instrument that allows independent control of irrigation and aspiration is needed. The instrument should prevent simultaneous activation of irrigation and aspiration. The instrument should provide convenient access to an actuator for controlling irrigation and aspiration. The instrument should enable precise flow control from extremely low to maximum flow rates.

An instrument that allows viewing of aspirated substances is also needed. The instrument should enable a user to determine if aspirated effluent is clear or includes entrained blood, bio burden or infectious matter.

The invention is directed to overcoming one or more of the problems and solving one or more of the needs as set forth above.

SUMMARY OF THE INVENTION

To solve one or more of the problems set forth above, in an exemplary implementation of the invention, a suction and irrigation implement includes a handpiece, a pair of aligned adjacent valve assemblies, a rocker and a hub. The handpiece includes a hollow handle and a body. An irrigation line and a suction line extend through the hollow handle to the valve assemblies. The body includes a lumen in fluid communication with each of the valve assemblies and the hub. The body may be transparent to allow visualization of aspirated substances. The valve assemblies include a plunger with a conical core that increases the area of the valve opening with increased depression of the plunger, thereby allowing precise flow control even at low flow rates. The rocker, a pivoting actuator, opens one valve assembly at a time, thereby preventing simultaneous irrigation and suction. The hub includes a central channel aligned with the lumen of the body. A suction and irrigation tube connects to the hub. The hub may be rotated to adjust the orientation of the tube, while the implement is in use. Detents define specific orientations.

In one embodiment, a handheld medical suction and irrigation implement includes a handpiece having a body and a lumen. The lumen extends to an open end of the body. Separate aligned adjacent first and second valve mechanisms are provided in fluid communication with the lumen. Each valve mechanism includes a port for fluidly coupling to a line such as a suction line or a liquid supply line. Each valve mechanism provides a fluid flow path between the port and the lumen when the valve mechanism is actuated (e.g., opened). An actuator includes a first portion that reaches the first valve mechanism and a second portion that reaches the second valve mechanism. A pivot point (i.e., structure that allows pivoting motion of the actuator) is provided between the first portion of the actuator and the second portion of the actuator. The actuator is finger manipulable and pivotable (i.e., capable of being pivoted in either direction using one or more fingers) from a neutral position to a first actuation range, and from a neutral position to a second actuation range. The first valve mechanism and the second valve mechanism are not actuated when the actuator is in the neutral position. The first valve mechanism is actuated and the second valve mechanism is not actuated when the actuator is in the first actuation range. The second valve mechanism is actuated and the first valve mechanism is not actuated when the actuator is in the second actuation range. Each actuation range includes a continuum of positions from an actuation minimum (e.g., corresponding to minimal valve opening) to an actuation maximum (e.g., corresponding to maximum valve opening). The volume of the fluid flow path between a port and the lumen increases as the actuator pivots from the actuation minimum towards the actuation maximum, e.g., the open passage through which fluid may flow increases.

The handpiece includes a hollow handle with an end cap. The end cap includes a first line aperture and a second line aperture. The first line aperture is configured to receive a suction line or a liquid supply line. The second line aperture is configured to receive the other of a suction line or the liquid supply line. In this manner, the lines run through the handle. This facilitates handling of the implement with attached lines.

The actuator may be a rocker assembly. The pivot point of the rocker assembly including a shaft. The handpiece includes a bearing fixed between the first valve mechanism and the second valve mechanism. The shaft is at least partially received in the bearing. The bearing may be a hollow cylinder, which may be formed as a first standing boss. The shaft may be a hollow cylinder, which also may be formed as a standing boss. To access the shaft for installation in the bearing, the rocker assembly may include a removable panel and a rocker body with the shaft being attached to the rocker body. In another embodiment, the bearing is formed in the rocker assembly and the shaft is fixed between the first valve mechanism and the second valve mechanism. Also, in each embodiment, the shaft may fit within the bearing, or the bearing may fit within the shaft. In each embodiment, the parts mate to allow pivoting movement of the shaft relative to the bearing.

Each valve mechanism includes a valve body with a valve body channel extending through the valve body. The valve mechanism also includes a spring and a plunger. The plunger is movable linearly within the valve body channel. The spring biases the plunger to a position that blocks fluid flow between the port and the lumen. Depressing a plunger opens the valve mechanism, allowing fluid flow therethrough. Flow rate is a function of the amount by which a plunger is depressed, with increased depression providing increased flow rate. Each plunger may have a plurality of O-rings installed, i.e., spaced apart O-rings with each O-ring being movable with the plunger and providing a fluid tight seal between the valve body and the plunger. Each valve body may be integrally formed parts of the handpiece or components (e.g., separate parts) attachable to the handpiece.

The implement also includes a hub that is removably and rotatably attached at the open end of the body. The hub has a central channel aligned with the lumen of the body. A tube may be attached to the hub. The hub is rotatable to adjust the orientation of the tube relative to the body.

BRIEF DESCRIPTION OF THE DRAWINGS

The foregoing and other aspects, objects, features and advantages of the invention will become better understood with reference to the following description, appended claims, and accompanying drawings, where:

FIG. 5 is a first perspective view of an exemplary handpiece of a medical implement for aspirating and irrigating according to principles of the invention; and FIG. 6 is a first perspective section view of an exemplary handpiece of a medical implement for aspirating and irrigating according to principles of the invention; and FIG. 7 is a first perspective view of an exemplary end cap for a handpiece of a medical implement for aspirating and irrigating according to principles of the invention; and FIG. 8 is a first perspective section view of an exemplary end cap for a handpiece of a medical implement for aspirating and irrigating according to principles of the invention; FIG. 13 is a first perspective view of an exemplary valve body for a medical implement for aspirating and irrigating according to principles of the invention; and FIG. 14 is a first perspective section view of an exemplary valve body for a medical implement for aspirating and irrigating according to principles of the invention.

Those skilled in the art will appreciate that the figures are not intended to be drawn to any particular scale; nor are the figures intended to illustrate every embodiment of the invention. The invention is not limited to the exemplary embodiments depicted in the figures or the specific components, configurations, shapes, relative sizes, ornamental aspects or proportions as shown in the figures. For convenience of reference, location terms such as top, bottom, up and down, upper and lower, and the like, may be used in this application to refer to a relative position and/or arrangement shown in one or more of the various drawings, and are not intended to restrict positioning or orientation of a product according to principles of the invention, or of any component thereof, during manufacture or in actual use.

DETAILED DESCRIPTION

A medical implement for irrigating and aspirating according to principles of the invention includes a handpiece, a pair of aligned adjacent valve assemblies, a rocker and a hub. The handpiece includes a hollow handle and a body. An irrigation line and a suction line extend through the hollow handle to the valve assemblies. The body includes a lumen in fluid communication with each of the valve assemblies and the hub. The body may be transparent to allow visualization of aspirated substances. The valve assemblies include a plunger with a conical core that increases the area of the valve opening with increased depression of the plunger. The rocker, a pivoting actuator, opens one valve assembly at a time, thereby preventing simultaneous irrigation and suction. The hub includes a central channel aligned with the lumen of the body. A suction and irrigation tube connects to the hub. The hub may be rotated to adjust the orientation of the tube, while the implement is in use. Detents define specific orientations.

Figure 1:
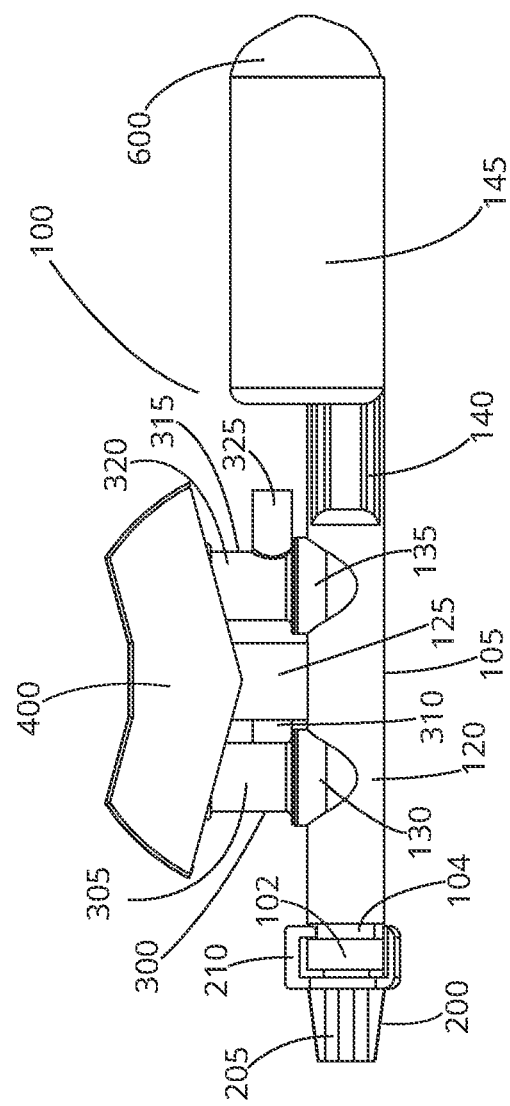
FIG. 1 is a front view of an exemplary medical implement for aspirating and irrigating according to principles of the invention.
Figure 2:
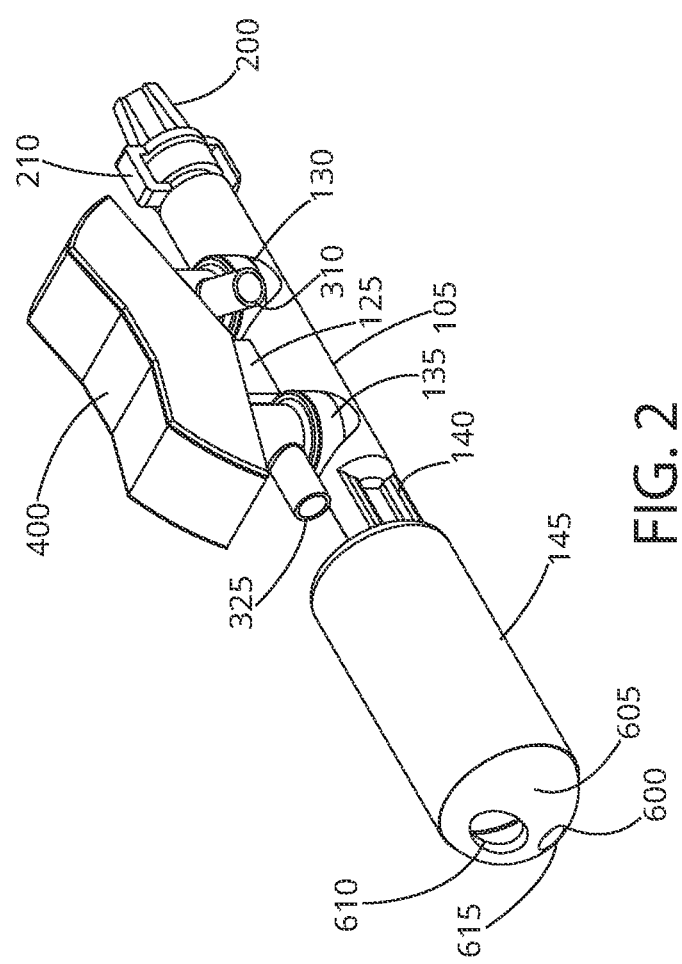
FIG. 2 is a first perspective view of an exemplary medical implement for aspirating and irrigating according to principles of the invention.

FIGS. 1 and 2 conceptually illustrate an exemplary medical implement 100 for aspirating and irrigating according to principles of the invention. Valve assemblies 300, 315, a hub 200, a rocker 400 and an end cap 600 mount to a handpiece 105.

The handpiece 105 includes a hollow handle 145, with a cavity 146, a hollow tubular body 120, with a lumen 107, a pair of valve ports 130, 135 and a neck 140. The neck 140 connects the handle 145 to the body 120. The end cap 600 covers the end of the handle 145 opposite the neck 140. The end cap 600 includes a concave body 605 with a pair of spaced apart apertures 610, 615 for receiving supply lines. The end of the handle 145 includes a counterbore 147 that receives a collar 605 of the end cap 600. The collar 605 also includes a pair of locator ribs 606 that slide into locator slots 148, 149 in the counterbore 147 to orient the apertures 615, 620 in alignment with apertures 616, 621.

The body 120 is a manifold with two inlets (i.e., valve ports 130, 135) and one outlet at the open end 102. A lumen 107 (FIG. 6), i.e., a channel through which fluid may flow, extends through the body 120. The end of the body 120 adjacent to the handle 145 is closed, while the opposite end 102 is opened. The hub 200 includes a cantilever hook 210, which engages an annular groove 104 for locking engagement to said opposite end 102. Said opposite end 102 is also referred to as the open end or distal end of the body 120 of the handpiece 105. Valve ports 130, 135 receive valve assemblies 300, 315, which independently control irrigating and aspirating flows. Each valve assembly 300, 315 includes a valve body 305, 320 with supply inlets 310, 325, which generally form tee fittings. Fluid flow paths extend from the hub 200, through the open end 102 of the body 120, through the lumen 107 of the body 120, through the valve ports 130, 135, through each valve body 305, 320, to the supply inlets 310, 325.

Figure 3:
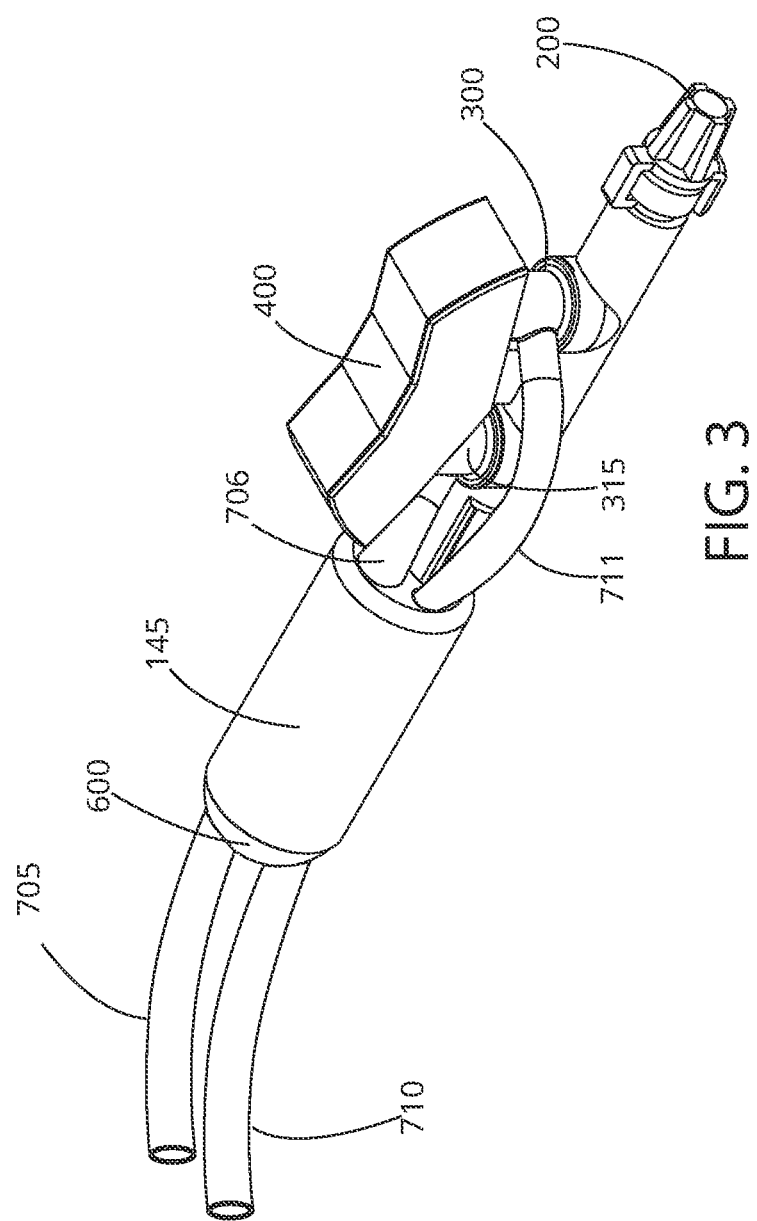
FIG. 3 is a second perspective view of an exemplary medical implement for aspirating and irrigating according to principles of the invention, with supply lines for irrigation and suction.
Figure 18:
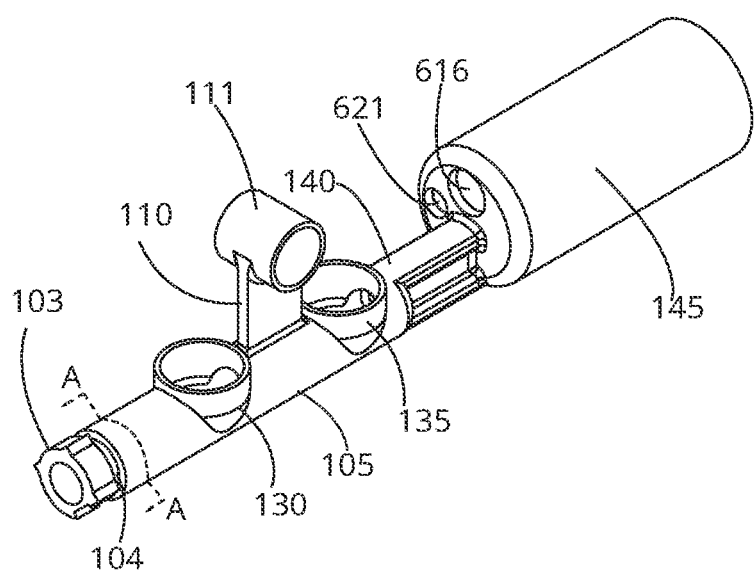
FIG. 18 is a perspective view of an exemplary alternative handpiece for a medical implement for aspirating and irrigating according to principles of the invention.
Figure 19:
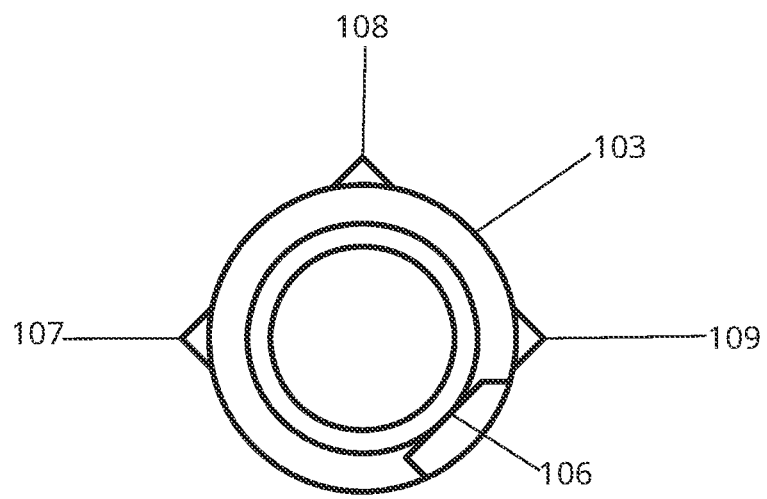
FIG. 19 is a side view of an exemplary hub-mount end (A-A) of a handpiece for a medical implement for aspirating and irrigating according to principles of the invention.
Figure 20:
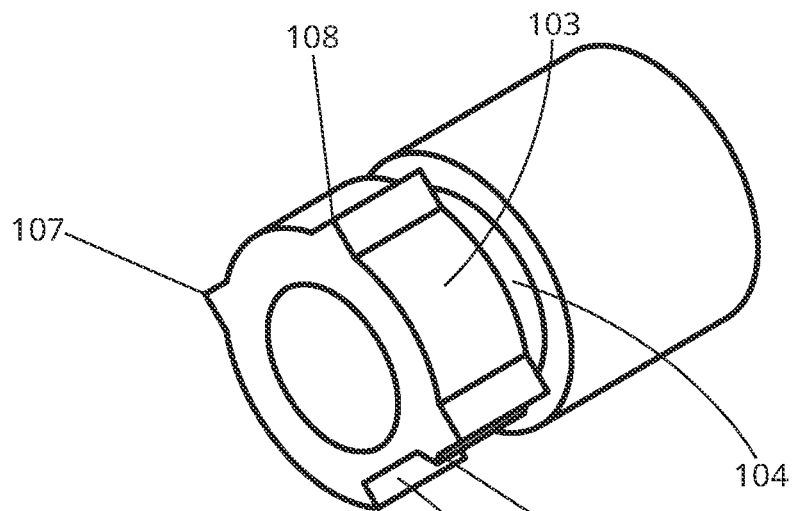
FIG. 20 is a first perspective view of the exemplary hub-mount end of a handpiece for a medical implement for aspirating and irrigating according to principles of the invention.
Figure 21:
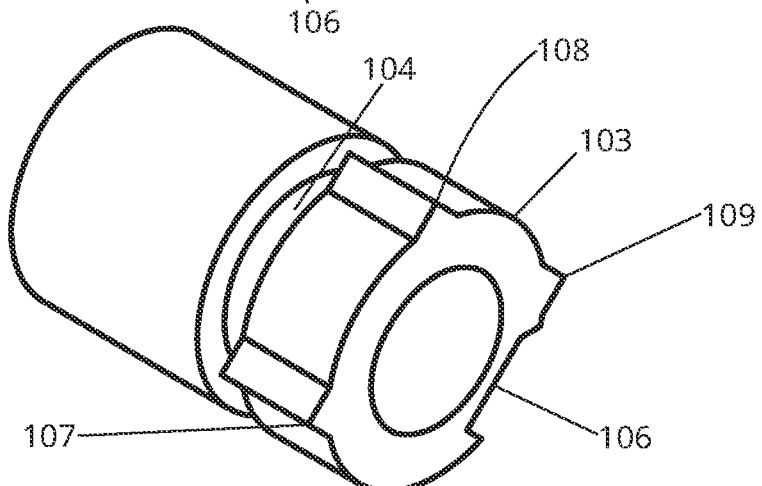
FIG. 21 is a second perspective view of the exemplary hub-mount end of a handpiece for a medical implement for aspirating and irrigating according to principles of the invention.
Figure 22:
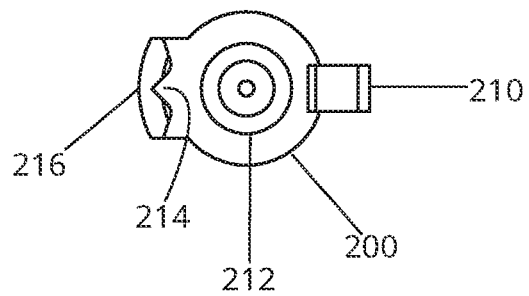
FIG. 22 is a side view of an exemplary hub for a medical implement for aspirating and irrigating according to principles of the invention.
Figure 23:
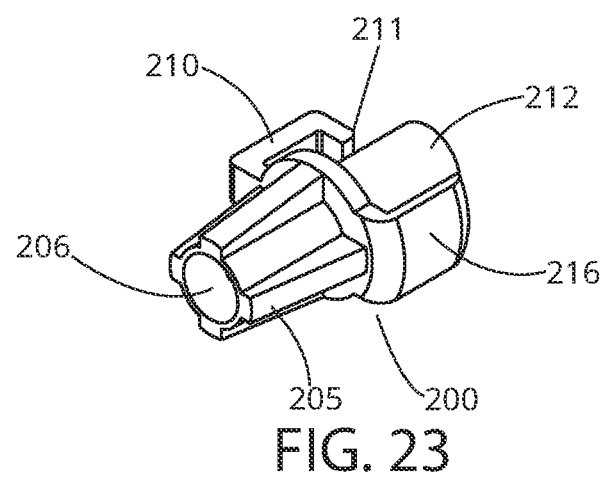
FIG. 23 is a first perspective view of an exemplary hub for a medical implement for aspirating and irrigating according to principles of the invention.
Figure 24:
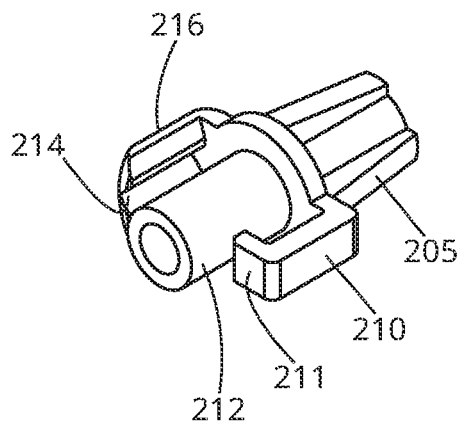
FIG. 24 is a second perspective view of an exemplary hub for a medical implement for aspirating and irrigating according to principles of the invention.
Figure 25:
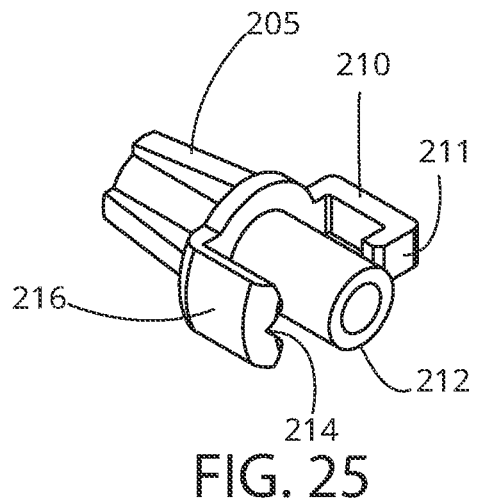
FIG. 25 is a third perspective view of an exemplary hub for a medical implement for aspirating and irrigating according to principles of the invention.

FIG. 3 conceptually illustrates the exemplary medical implement 100 with irrigation and suction supply lines 705, 710. The lines 705, 710 extend through the apertures 610, 615 in the end cap 605, through the handle 145, and to the supply inlets 310, 325. As more clearly visible in FIGS. 6 and 18, ends 706, 711 of the supply lines 705, 710 extend through apertures 616, 621 in the end of the handle 145 adjacent to the neck 140. These ends 706, 711 connect to the supply inlets 310, 325.

Fluid flow may proceed in either direction through each supply lines 705, 710. The direction of flow is determined by the source. For example, a pressurized liquid source may supply water to a valve inlet, while a suction source may draw (aspirate) fluid from the valve inlet.

Figure 4:
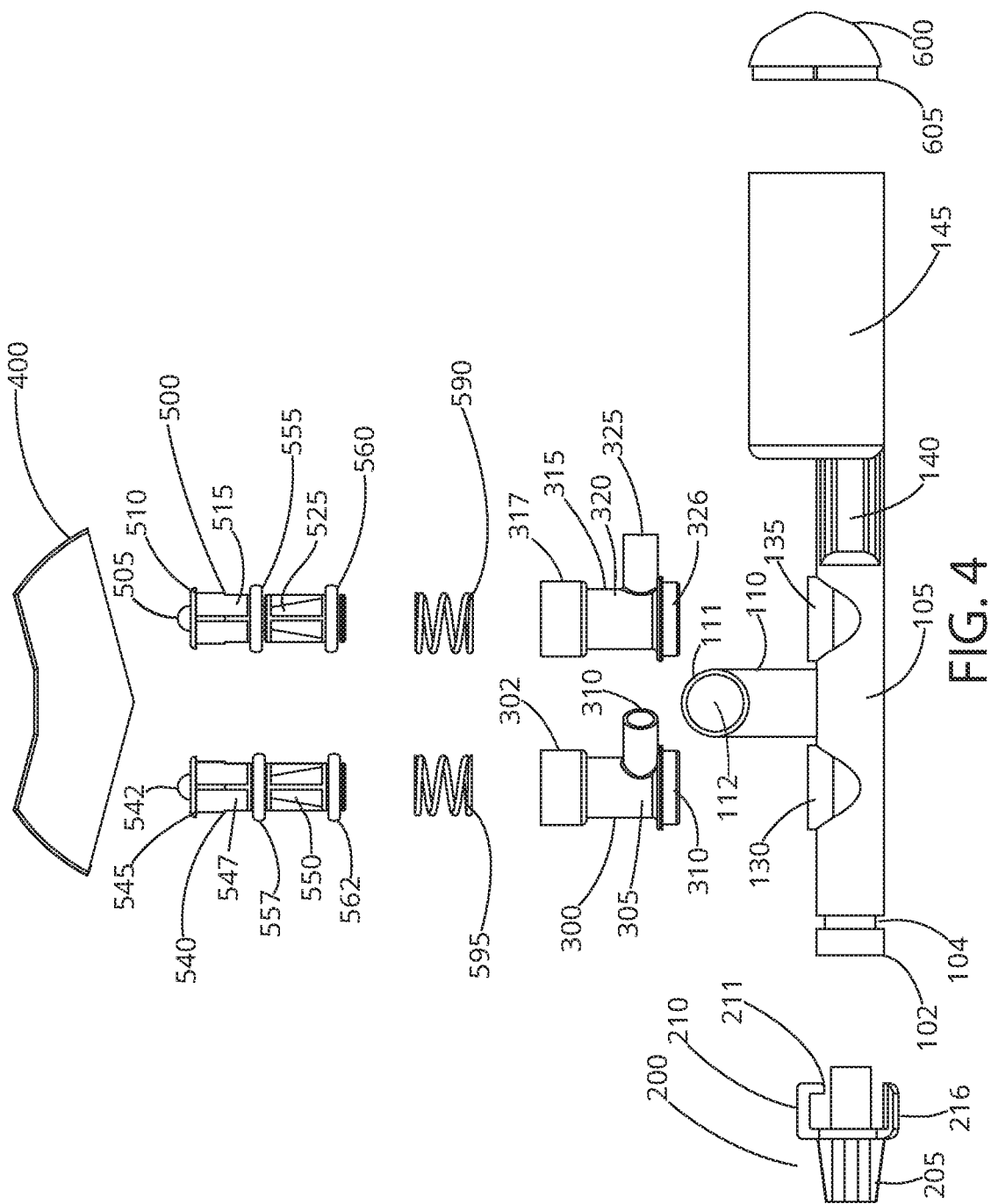
FIG. 4 is a front exploded view of an exemplary medical implement for aspirating and irrigating according to principles of the invention.
Figure 12:
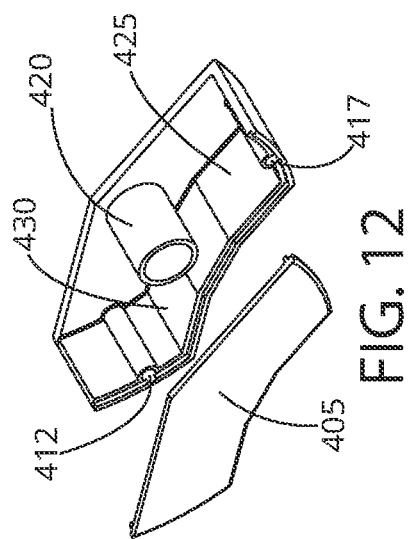
FIG. 12 is a second perspective section view of an exemplary rocker for a medical implement for aspirating and irrigating according to principles of the invention.

The exploded view of FIG. 4 reveals exemplary valve assembly components, a rocker fulcrum and other components and aspects of the implement 100. The rocker fulcrum includes a leg 110 and a bearing 111. The leg 110 extends from the body 105, between the valve ports 130, 135. The leg 110 supports the bearing 111 at a determined distance from the surface of the body 105. The distance allows contact surfaces 425, 430 (FIG. 12) of the rocker 400 to contact and depress plungers 500, 540 of the valve assemblies. The exemplary bearing 111, which is a hollow cylinder, formed as a standing boss at the free end of the leg 110, holds a rotating shaft of the rocker 400. Specifically, with reference to FIGS. 5, 6, 11 and 12, the bearing 111 receives, within the channel 112 defined by the bearing 111, a journal 420 (i.e., hollow shaft) within the rocker 400. The outer diameter of the journal 420 does not exceed the inner diameter of the bearing 111 and, preferably, is slightly less (e.g., 0.1% to 5.0% less) than the inner diameter of the bearing 111. The rocker 400 may pivot relative to the fulcrum. To facilitate proper alignment, the exemplary rocker 400 includes a side panel with locator pins 410, 415 that are received in cylindrical channels within bosses 412, 417. A longitudinal axis of the leg 110 is perpendicular to a longitudinal axis of the body 105. A central axis of the bearing 111 is perpendicular to the longitudinal axis of the leg 110.

The implement includes two valve assemblies 300, 315. Each valve assembly 300, 315 includes a plunger 500, 540; compression spring 590, 595; and valve body 305, 320. The spring 590, 595 is disposed between an upper flange 510, 545 of the plunger 500, 540 and the bottom of a spring fairing 302, 317. The spring fairing 302, 317 is a hollow cylinder integrally formed with and extending from the valve body 305, 320, with a slightly greater inner diameter than the inner diameter of the valve body 305, 320. A fillet, chamfer or step 318 provides a transition between the bottom of the fairing 302, 317 and the body 305, 320.

Referring to FIGS. 13 and 14, each valve assembly 300, 315 includes a valve body 305, 320 with supply inlets 310, 325, which generally form tee fittings. Fluid flows through a channel in the inlet 310, 325 and through a channel 327 in the body 305, 320. The channel 318 in the fairing 317 receives a portion of the plunger 500.

Each valve body 305, 320 mates with a valve port 130, 135. The mating end of each valve body includes a skirt 326 sized and shaped to mate with the valve port 130, 135. The valve port 130, 135 receives the skirt 326 up to an exterior annular flange 323. Fluid flows to and from the valve body through channel 327 to and from the channel 132, 137 of the valve port 130, 135.

Figure 9:
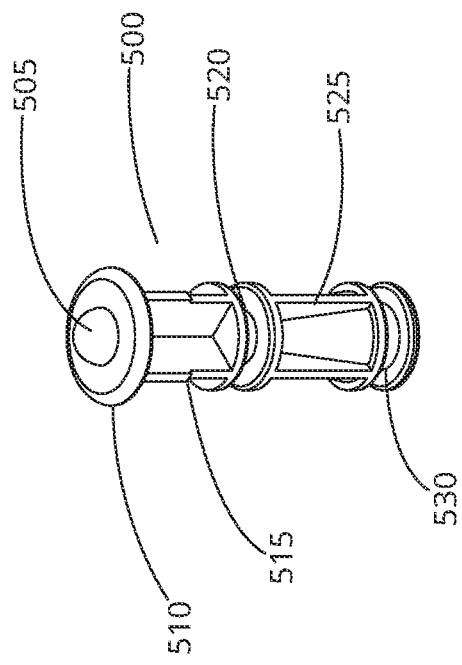
FIG. 9 is a first perspective view of an exemplary plunger for a valve of a medical implement for aspirating and irrigating according to principles of the invention.
Figure 10:
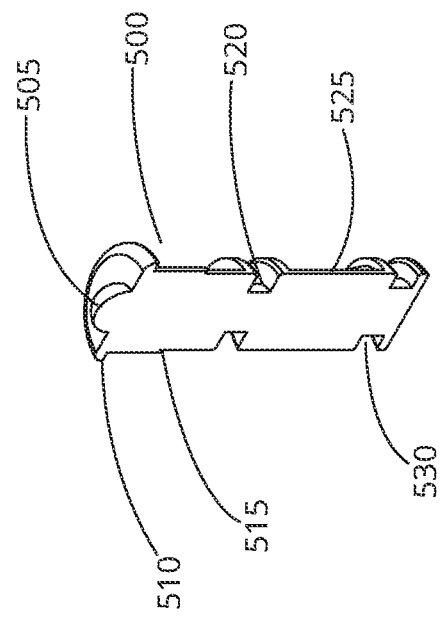
FIG. 10 is a first perspective section view of an exemplary plunger for a valve of a medical implement for aspirating and irrigating according to principles of the invention.
Figure 11:
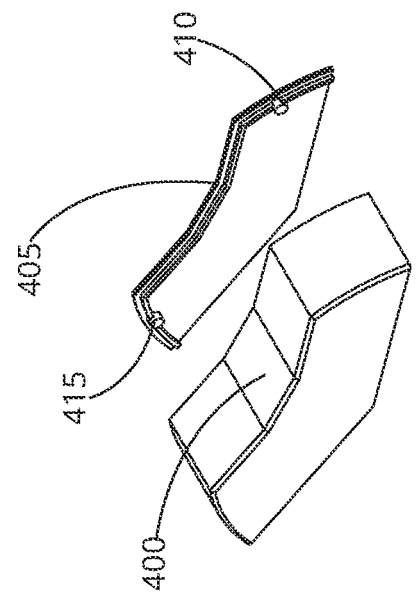
FIG. 11 is a first perspective exploded view of an exemplary rocker for a medical implement for aspirating and irrigating according to principles of the invention.

The exemplary implement includes two identical valve assemblies 300, 315. With reference to FIGS. 9, 10, each valve assembly 300, 315 includes a plunger 500, 540 sized and shaped to be slidingly disposed within the fairing 302, 317 and body 305, 320, with portions of the plunger extending from the fairing 302, 317 and body 305, 320. A hemispherical tip 505, 542 provides a contact point for the contact surfaces 425, 430 of the rocker 400. Depressing a tip 505, 542 depresses the plunger 500, 540. An upper flange 510, 545 provides a surface to engage the top of the compression spring 590, 595. An upper portion 515, 547 extends downward from the upper flange 510 to the intermediate annular groove 520. The intermediate annular groove 520 is a furrow defined between parallel spaced apart flanges. The groove 520 provides a space for receiving an elastomeric O-ring 555, 557. When installed, the outer diameter of the O-ring 555, 557 provides a fluid tight seal against the interior wall of the valve body 305, 320. A variable diameter (i.e., conical core) valve member 525, 550 provides a movable obstruction within and adjustably restricts flow through the valve body 305, 320. The valve member extends downward to a lower annular groove 530. The intermediate annular groove 530 is a furrow defined between parallel spaced apart flanges. The groove 530 provides a space for receiving an elastomeric O-ring 560, 562. When installed, the outer diameter of the O-ring 560, 562 provides a fluid tight seal against the interior wall of the transition between the bottom skirt 312, 326 and the valve body 305, 320, when the valve assembly is closed, thereby preventing flow through the valve assembly 300, 315.

Each valve assembly 300, 315 includes a compression spring 590, 595. The spring 590, 595 urges the plunger 500, 515 into a closed position, with the bottom O-ring 560, 562 providing a fluid tight seal against the interior wall of the transition between the bottom skirt 312, 326 and the valve body 305, 320, and the intermediate O-ring 555, 557 providing a fluid tight seal against the interior wall of the valve body 305, 320 above the inlet 310, 325. The top of the spring 590, 595 abuts the underside of the upper flange 510. The bottom of the spring 590, 595, abuts the bottom of the spring fairing 302, 317, at the top of the valve body 305, 320.

Figure 15:
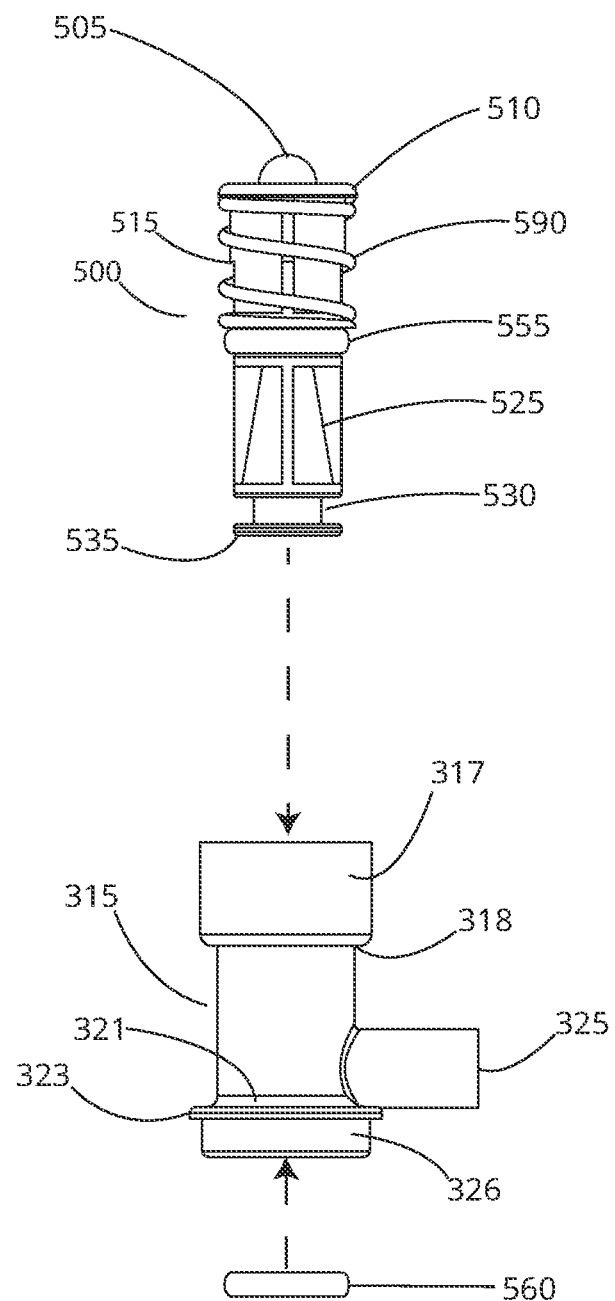
FIG. 15 is a front exploded view of an exemplary valve assembly for a medical implement for aspirating and irrigating according to principles of the invention.
Figure 16:
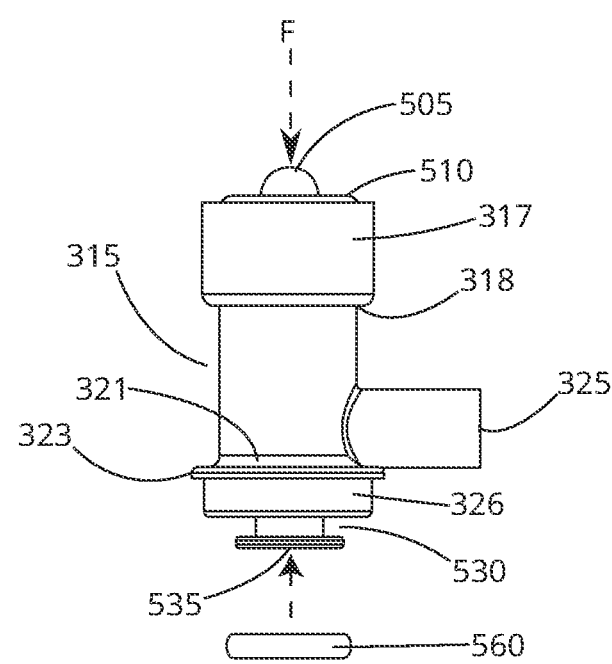
FIG. 16 is a front partially assembled view of an exemplary valve assembly for a medical implement for aspirating and irrigating according to principles of the invention.
Figure 17:
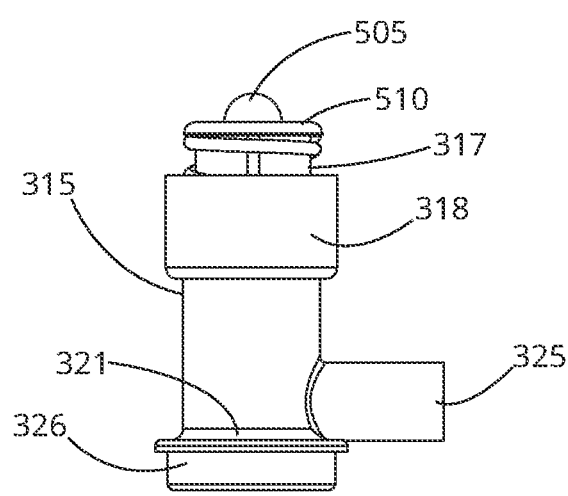
FIG. 17 is a front assembled view of an exemplary valve assembly for a medical implement for aspirating and irrigating according to principles of the invention.

FIGS. 15 through 17 conceptually illustrate steps of assembling an exemplary valve assembly for a medical implement for aspirating and irrigating according to principles of the invention. The spring 590 is slid onto the plunger 500, surrounding the upper portion 515, abutting the flange 510. The intermediate O-ring 555 is installed. The bottom O-ring 560 is not yet installed. In FIG. 16, the plunger 500 with the spring 590 and O-ring 555 is inserted into the valve body 315. As force (F) is applied to the tip 505 (FIG. 16), the bottom of the spring 590 abuts the interior of the transition 318 at the bottom of the fairing 317 and the spring 590 compresses. The diameter of the spring 590 is too big for the spring to progress downward beyond the transition 318. The plunger 500 is sized for the annular groove 530 to extend from the skirt 326, when the tip 505 is pressed downward and the spring 590 is compressed, until the bottom annular groove 530 extends from the bottom of the skirt 326. The bottom O-ring 560 is then installed on the plunger 500 at the bottom annular groove 530. Then the tip 505 is released (i.e., no longer pressed). The bottom O-ring 560 is drawn into the skirt 326 (FIG. 17). The bottom O-ring 560 prevents the spring 590 from dislodging the plunger 500 from the body 315, because the bottom O-ring cannot pass beyond the transition 321 at the top of the skirt 326. Thus, the O-ring 560 captures the plunger 500 in the valve body 315. This assembly, valve assembly, may then be mounted to the handpiece 105 by inserting the skirt 326 in a valve port 130, 135. The valve assembly may be permanently bonded to the valve port 130, 135 by chemical bonding agent, ultrasonic welding, or other bonding technique for joining plastic parts.

In one exemplary embodiment, the open end of the handpiece and the hub are configured to achieve various orientations of the hub relative to the open end, by rotating the hub relative to the free end. A user may select a convenient orientation for a procedure, without extreme wrist rotation. The free end 103 of the handpiece in FIGS. 18-21, includes a plurality of wedge detents 107-109, and a groove 106. While three wedge detents are shown, the invention is not limited to any particular number of wedge detents, detents having a wedge shape, or having any detents. The groove receives the tip 211 (FIGS. 22-25) of the cantilever hook 210 to facilitate installation. A V-shaped groove 214 in the guide 216 receives a wedge 107-109 to releasably lock the hub 200 in an orientation relative to the handpiece. The guide is a flexible tab opposite the cantilever hook 210. Deflection of the guide 216 allows releasing the hub. The base 212 of the hub 200 is a hollow tube that mates with the free end of the handpiece 105.

Figure 26:
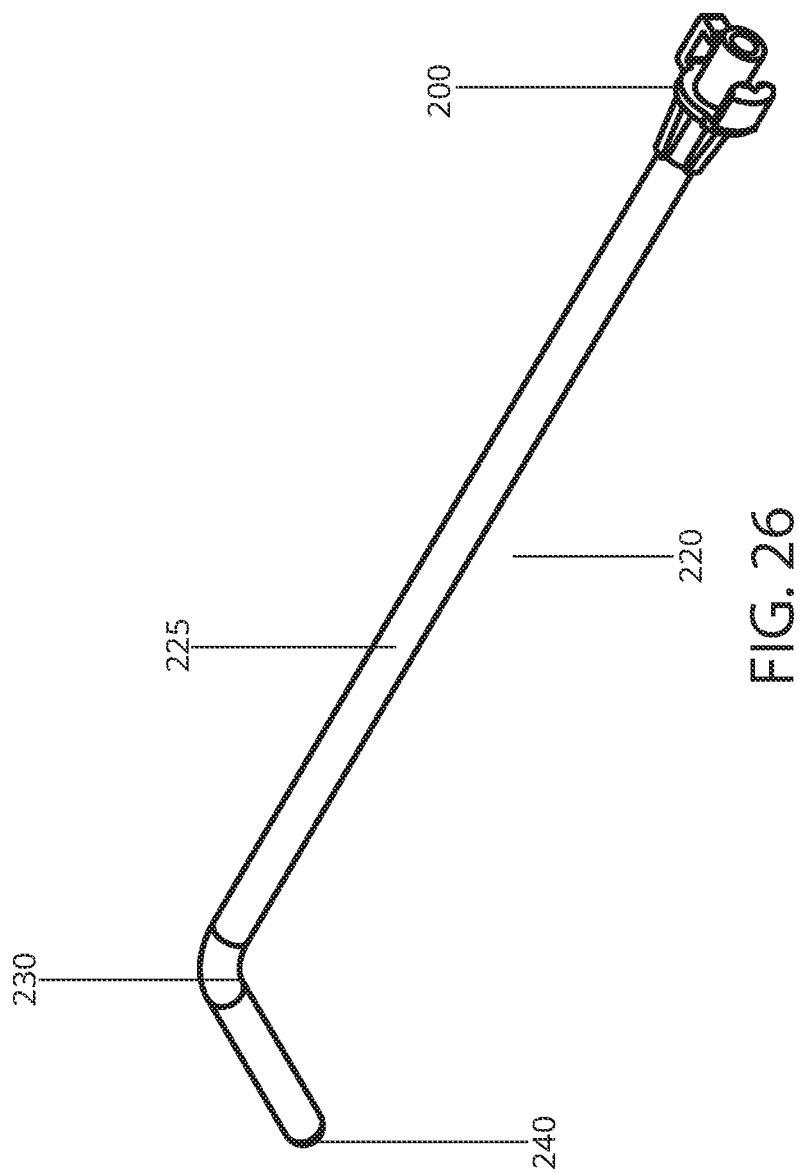
FIG. 26 is a perspective view of an exemplary hub and irrigation/suction tube for a medical implement for aspirating and irrigating according to principles of the invention.

The instrument mounting end 205 of the hub 200 includes a socket 206 that receives the end of a tube 220 (FIG. 26) for a procedure. The exemplary tube 220 includes a straight segment 225, a bend 230 and a tip 240, through which fluid may be ejected or aspirated. Such tubes come in a variety of shapes and dimensions. The invention is not limited to any particular tube size, shape or configuration. The tube 220 may be permanently or removably coupled to the socket 206 of the hub 200.

Figure 27:
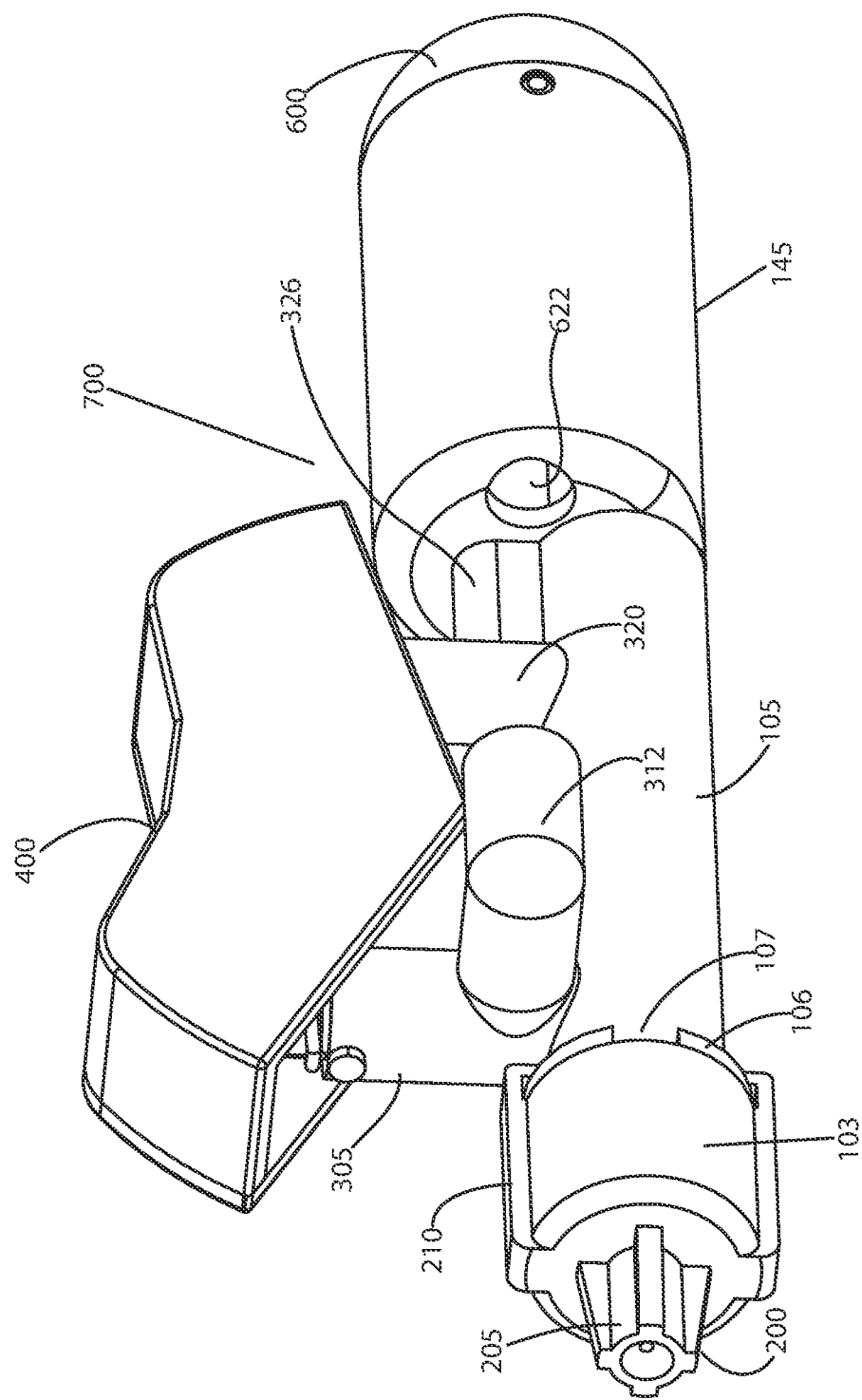
FIG. 27 is a perspective view of another exemplary medical implement for aspirating and irrigating according to principles of the invention.
Figure 28:
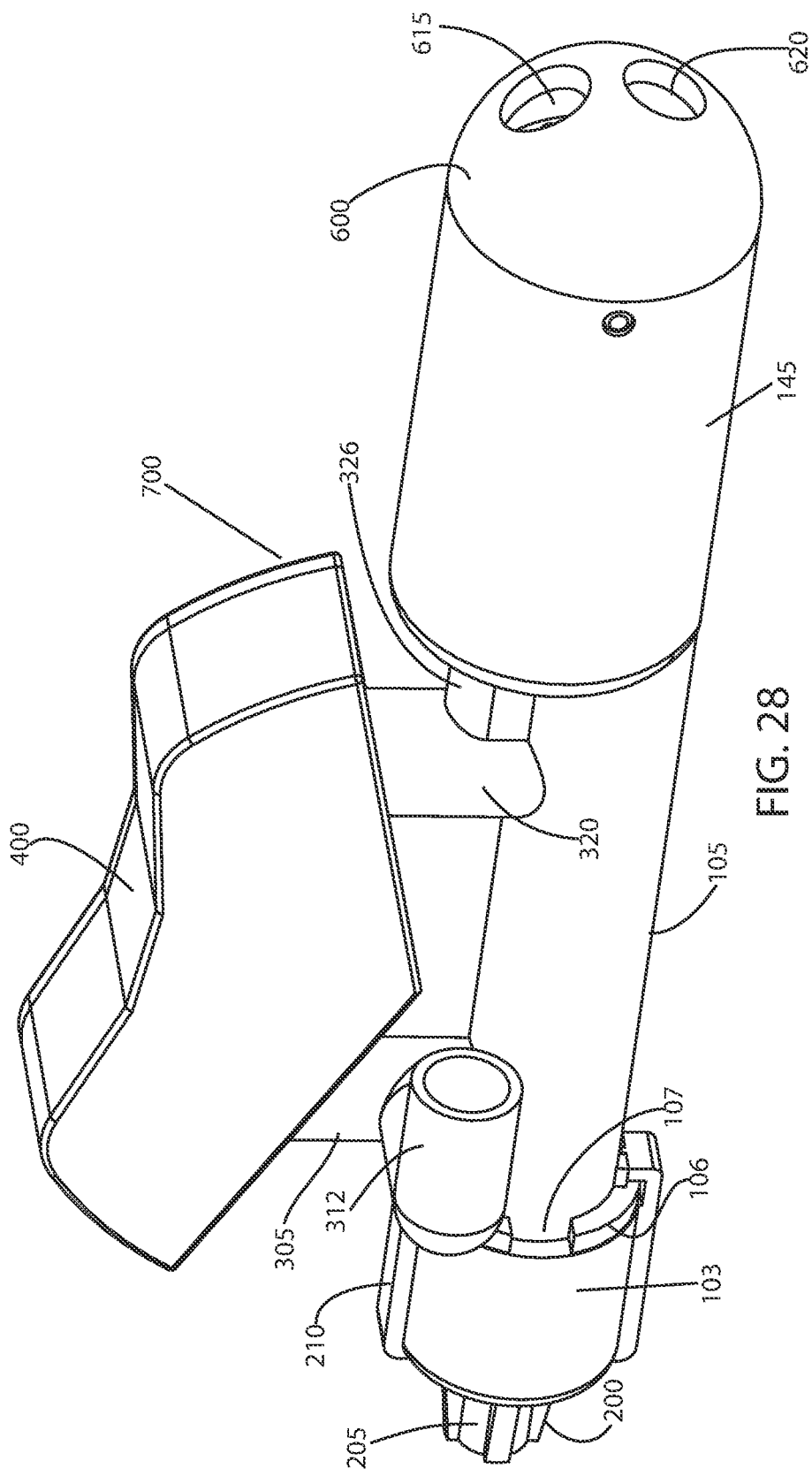
FIG. 28 is another perspective view of the exemplary medical implement of FIG. 27.
Figure 29:
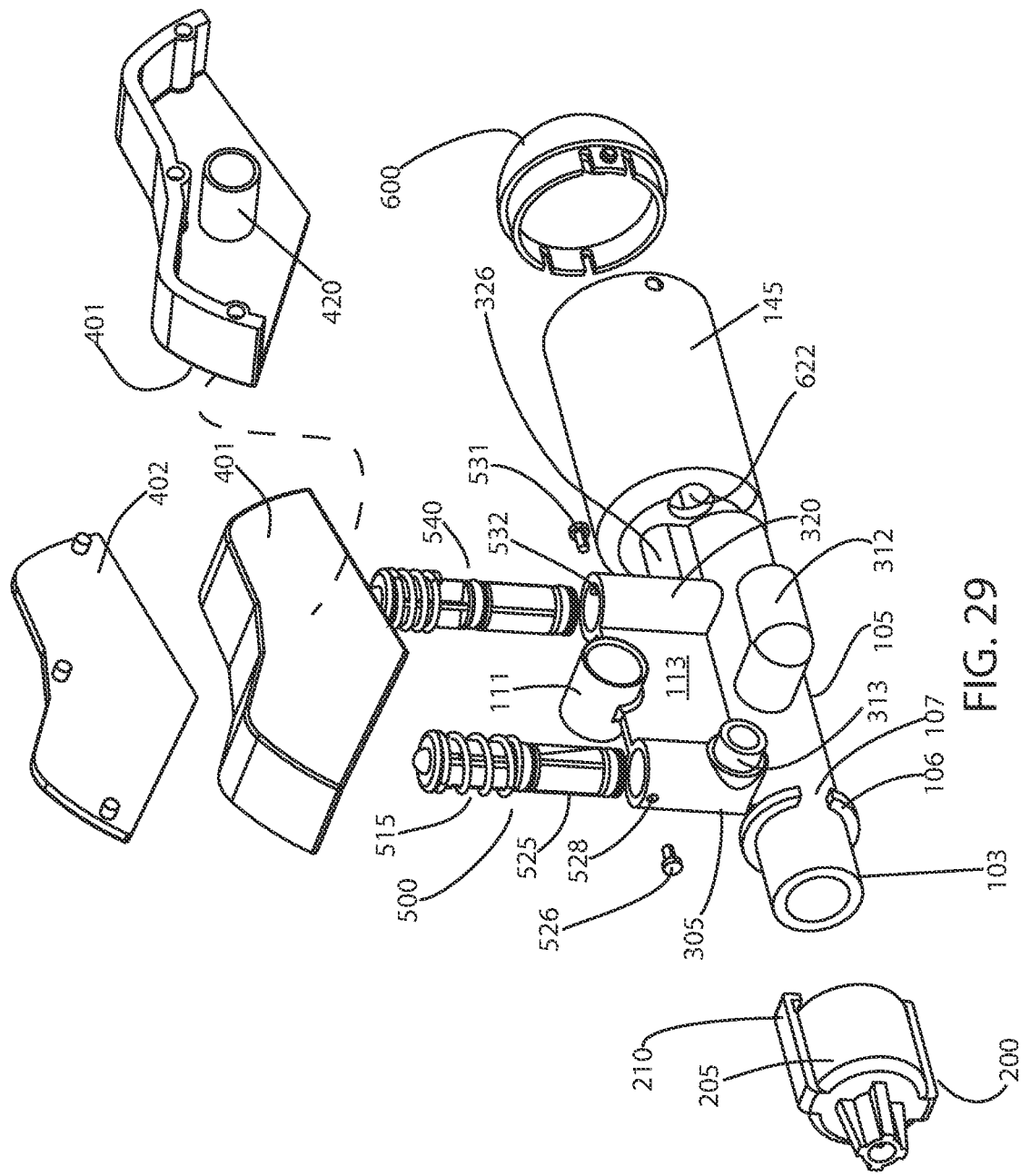
FIG. 29 is an exploded perspective view of the exemplary medical implement of FIG. 27.

FIGS. 27-29 conceptually illustrate another exemplary medical implement for aspirating and irrigating according to principles of the invention. In this embodiment, the hub 200 includes a pair of cantilever hooks 210, which engages an annular flange 106 for locking engagement to said opposite end 102, i.e., the open end or distal end of the handpiece 105. A pair of opposed gaps 107 in the flange 106 allow passage of the tips of the cantilever hooks 210 for mating engagement.

In this embodiment, the valve bodies 305, 320 are integrally formed with the handpiece 105. An elbow 312 and annular flange 313 provide a fluid coupling to valve body 305. A hose (e.g., fluid supply line) may extend through an aperture 620 in end cap 600, along furrow 149, through aperture 622, through cavity 146, and connect to elbow 312, which connects to annular flange 313, which is coupled to the valve body 305, thus providing a fluid flow path between a hose and valve body 305.

The handpiece 105 includes a hollow handle 145. The end cap 600 includes an aperture 615 through which another hose may extend. The hose may extend to coupling 329. Thus, a fluid flow path is provided through the hose, the channel 328 of the coupling 329, and the channel 327 of an inlet 326 coupled to valve body 320. In this embodiment, the inlet 326 and coupling 329 are integral parts of the handpiece 105.

Figure 30:
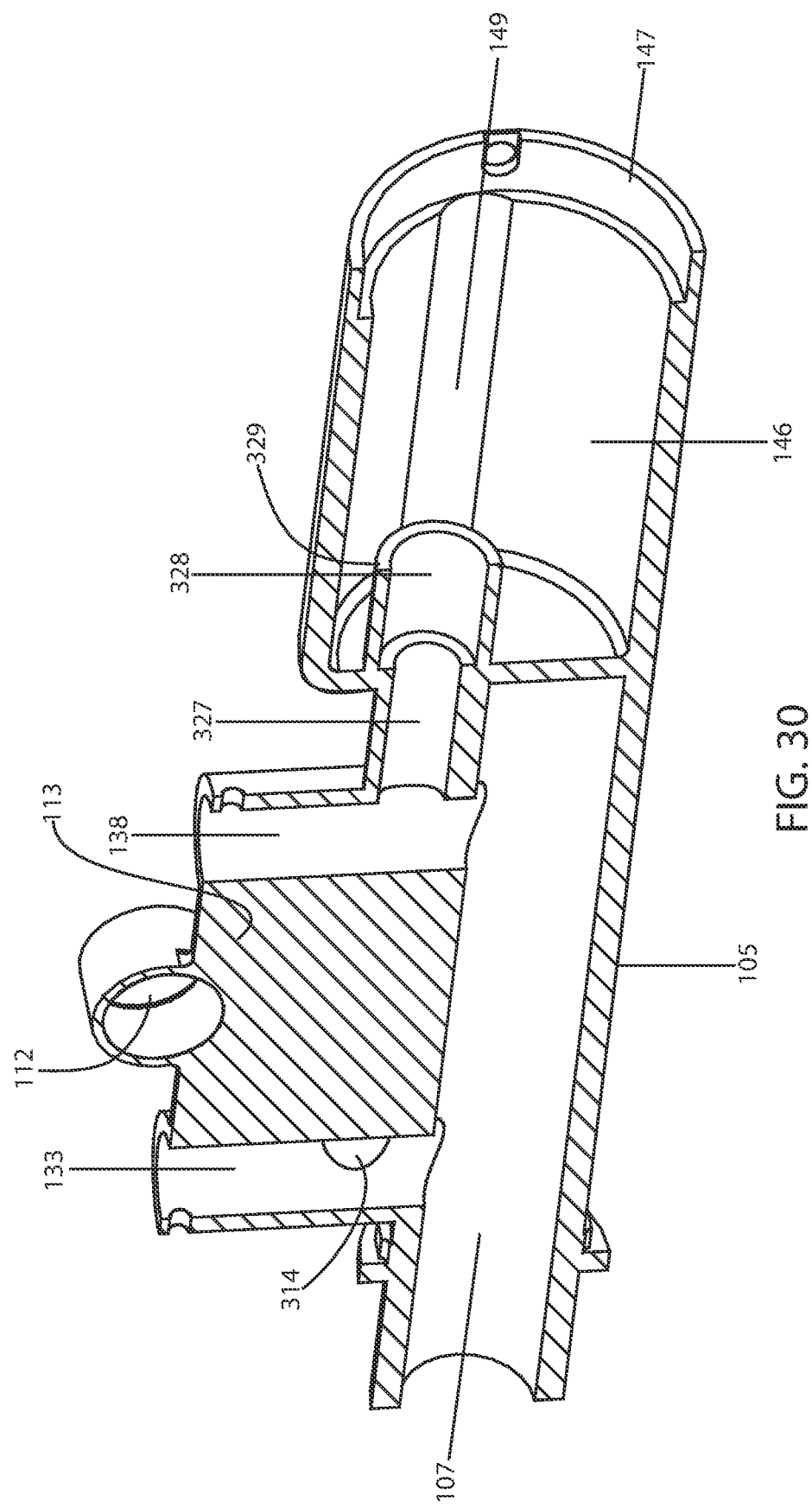
FIG. 30 is a section perspective view of a handpiece for the exemplary medical implement of FIG. 27.

FIG. 30 is a section perspective view of a handpiece 105 for the exemplary medical implement of FIG. 27. Flow paths between hub 200 and end cap 600, through each valve body 305, 320 are shown. A lumen 107, i.e., a channel through which fluid may flow, extends through the body 120. A central cavity 146 is provided within the handle 145. Each valve body 305, 320 includes a central channel 133, 138, respectively.

A rocker fulcrum includes a panel 113 and a bearing 111. The panel 113 extends from the body 105, between the valve bodies 305, 320. The panel 113 supports the bearing 111 at a determined distance from the surface of the body 105. The distance allows contact surfaces 425, 430 (FIG. 12) of the rocker 400 to contact and depress plungers 500, 540 of the valve assemblies 500, 540. The exemplary bearing 111, which is a hollow cylinder, formed as a standing boss at the free end of the panel 113, holds a rotating shaft 420 of the rocker 400. Specifically, the bearing 111 receives, within the channel 112 defined by the bearing 111, a journal 420 (i.e., hollow shaft) within the rocker 400. The outer diameter of the journal 420 does not exceed the inner diameter of the bearing 111 and, preferably, is slightly less (e.g., 0.1% to 5.0% less) than the inner diameter of the bearing 111. The rocker 400 may pivot relative to the fulcrum. To facilitate proper alignment, the exemplary rocker 400 includes a rocker body 401 and side panel 402 with locator pins 410, 415 (FIGS. 11 & 12) that are received in cylindrical channels within bosses 412, 417. A longitudinal axis of the panel 113 is perpendicular to a longitudinal axis of the body 105. A central axis of the bearing 111 is perpendicular to the longitudinal axis of the panel 113.

A stop 526, 531 is provided for each valve body 305, 320. Each stop has a shank extending from a head. The shank extends through a hole 528, 532 in the valve body 305, 320, until the head abuts the valve body 305, 320. The shank of each stop 526, 531, prevents ejection of the spring-biased valve assembly 500, 540 from each valve body 305, 320.

A device according to principles of the invention thus provide a medical practitioner, such as an otolaryngologist or a neurosurgeon, a tool for aspirating fluid and/or debris and/or irrigating fluid and/or medicants during surgical procedures. The rocker allows convenient selection of either suction or irrigation, one at a time, but not both suction and irrigation simultaneously. The rocker and valve assemblies also allow variable flow control. The degree to which a valve assembly is depressed in a valve body and the geometry of the core of the valve assembly determines the volume of the open flow path through the valve body. A conical core of each valve member facilitates variable flow control.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A handheld medical suction and irrigation implement comprising:

a handpiece comprising a body and a lumen, the lumen extending to an open end of the body; and a first valve mechanism in fluid communication with the lumen, the first valve mechanism including a first valve body attached to the handpiece, a first valve body channel extending through the first valve body from a first open end to the lumen, a first spring and a first plunger, at least a portion of the first plunger being received in and movable linearly within the first valve body channel, a first port for fluidly coupling to a suction line, the first port being fixed to the first valve body, the first spring biasing the first plunger to a position that blocks fluid flow between the first port and the lumen, and the first valve mechanism providing a fluid flow path between the first port and the lumen when the first plunger is urged toward the first spring and thereby compresses the first spring;

a first plurality of O-rings, including a first pair of spaced apart O-rings with each O-ring of the first pair being installed on the first plunger, movable with the first plunger and providing a fluid tight seal between the first valve body and the first plunger;

a second valve mechanism in fluid communication with the lumen, the second valve mechanism including a second valve body attached to the handpiece, a second valve body channel extending through the second valve body from a second open end to the lumen, a second spring and a second plunger, at least a portion of the second plunger being received in and movable linearly within the second valve body channel, a second port for fluidly coupling to a liquid supply line, the second port being fixed to the second valve body, the second spring biasing the second plunger to a position that blocks fluid flow between the second port and the lumen, the second valve mechanism providing a fluid flow path between the second port and the lumen when the second plunger is urged toward the second spring and thereby compresses the second spring, the second valve mechanism being aligned with, spaced apart from and adjacent to the first valve mechanism;

a rocker assembly, the rocker assembly including a first portion that reaches the first valve mechanism, and a second portion that reaches the second valve mechanism, and a shaft between the first portion of the rocker assembly and the second portion of the rocker assembly, and the rocker assembly being finger manipulable and pivotable from a neutral position to a first actuation range, and from a neutral position to a second actuation range; and a first standing boss fixed between the first valve mechanism and the second valve mechanism, the first standing boss comprising a leg extending from the body of the handpiece, between the first valve mechanism and the second valve mechanism, to a hollow cylinder, the hollow cylinder being attached to the leg, and the shaft of the rocker assembly being at least partially received in the hollow cylinder;

wherein the first valve mechanism and the second valve mechanism are not actuated when the rocker assembly is in the neutral position, and the first valve mechanism is actuated and the second valve mechanism is not actuated when the rocker assembly is in the first actuation range, and the second valve mechanism is actuated and the first valve mechanism is not actuated when the rocker assembly is in the second actuation range.

2. The handheld medical suction and irrigation implement of claim 1, wherein the first actuation range comprises a continuum of positions from a first actuation minimum to a first actuation maximum, and the volume of the fluid flow path between the first port and the lumen increasing as the rocker assembly pivots from the first actuation minimum towards the first actuation maximum; and the second actuation range comprises a continuum of positions from a second actuation minimum to a second actuation maximum, and the volume of the fluid flow path between the second port and the lumen increasing as the rocker assembly pivots from the second actuation minimum towards the second actuation maximum.

3. The handheld medical suction and irrigation implement of claim 1, wherein the handpiece includes a hollow handle with an end cap, and the end cap includes a first line aperture and a second line aperture, the first line aperture being configured to receive one of the suction line and the liquid supply line, and the second line aperture being configured to receive the other of the suction line and the liquid supply line.

4. The handheld medical suction and irrigation implement of claim 1, the shaft comprising a hollow cylinder.

5. The handheld medical suction and irrigation implement of claim 1, the rocker assembly comprising a removable panel and a rocker body, the shaft being attached to the rocker body.

6. The handheld medical suction and irrigation implement of claim 5, the shaft being a second boss.

7. A handheld medical suction and irrigation implement, comprising:

a handpiece comprising a body and a lumen, the lumen extending to an open end of the body; and a first valve mechanism in fluid communication with the lumen, the first valve mechanism including a first valve body with a first valve body channel extending through the first valve body, a first spring and a first plunger, the first plunger being movable linearly within the first valve body channel, a first port for fluidly coupling to a suction line, the first spring biasing the first plunger to a position that blocks fluid flow between the first port and the lumen, the first valve mechanism providing a fluid flow path between the first port and the lumen when the first valve mechanism is actuated;

a second valve mechanism in fluid communication with the lumen, the second valve mechanism including a second valve body with a second valve body channel extending through the second valve body, a second spring and a second plunger, the second plunger being movable linearly within the second valve body channel, a second port for fluidly coupling to a liquid supply line, the second spring biasing the second plunger to a position that blocks fluid flow between the second port and the lumen, the second valve mechanism providing a fluid flow path between the second port and the lumen when the second valve mechanism is actuated, the second valve mechanism being aligned with, spaced apart from and adjacent to the first valve mechanism;

a first plurality of O-rings, including a first pair of spaced apart O-rings with each O-ring of the first pair being installed on the first plunger, movable with the first plunger and providing a fluid tight seal between the first valve body and the first plunger;

a second plurality of O-rings, including a second pair of spaced apart O-rings with each O-ring of the second pair being installed on the second plunger, movable with the second plunger and providing a fluid tight seal between the second valve body and the second plunger;

a rocker assembly, the rocker assembly including a first portion that reaches the first valve mechanism and a second portion that reaches the second valve mechanism, and a shaft between the first portion of the rocker assembly and the second portion of the rocker assembly, and the rocker assembly being finger manipulable and pivotable from a neutral position to a first actuation range, and from a neutral position to a second actuation range; and a first standing boss fixed between the first valve mechanism and the second valve mechanism, the first standing boss comprising a leg extending from the body of the handpiece, between the first valve mechanism and the second valve mechanism, to a hollow cylinder, the hollow cylinder being attached to the leg, and the shaft of the rocker assembly being at least partially received in the hollow cylinder;

wherein the first valve mechanism and the second valve mechanism are not actuated when the rocker assembly is in the neutral position, and the first valve mechanism is actuated and the second valve mechanism is not actuated when the rocker assembly is in the first actuation range, and the second valve mechanism is actuated and the first valve mechanism is not actuated when the rocker assembly is in the second actuation range.

8. The handheld medical suction and irrigation implement of claim 7, wherein the handpiece includes a bearing fixed between the first valve mechanism and the second valve mechanism, and the shaft being at least partially received in the bearing.

9. The handheld medical suction and irrigation implement of claim 7, wherein the first valve body and second valve body are integrally formed parts of the handpiece.

10. The handheld medical suction and irrigation implement of claim 7, wherein the first valve body and second valve body are components attachable to the handpiece.

11. The handheld medical suction and irrigation implement of claim 7, further comprising a hub removably and rotatably attached at the open end of the body, the hub including a central channel aligned with the lumen of the body; and a tube attached to the hub, wherein the hub is rotatable to adjust the orientation of the tube relative to the body.

* * * * *